United States Patent [19]
Segalman et al.

[11] Patent Number: 5,795,581
[45] Date of Patent: Aug. 18, 1998

[54] CONTROLLED RELEASE OF MOLECULAR COMPONENTS OF DENDRIMER/BIOACTIVE COMPLEXES

[75] Inventors: Daniel J. Segalman; J. Shield Wallace, both of Albuquerque, N. Mex.

[73] Assignee: Sandia Corporation, Albuquerque, N. Mex.

[21] Appl. No.: 415,352

[22] Filed: Mar. 31, 1995

[51] Int. Cl.$^6$ .............................. A61K 9/00; A01N 25/00
[52] U.S. Cl. .................. 424/400; 424/405; 424/438; 424/439; 424/484; 424/485; 424/486; 424/487; 424/488; 424/489; 424/DIG. 16
[58] Field of Search .................. 424/DIG. 16, 449, 424/405, 422, 438, 439, 450, 484–489

[56] References Cited

U.S. PATENT DOCUMENTS

| | | | |
|---|---|---|---|
| 5,324,750 | 6/1994 | Lincoln et al. | 514/570 |
| 5,366,961 | 11/1994 | Harrington | 514/53 |
| 5,470,307 | 11/1995 | Lindall | 604/20 |

*Primary Examiner*—Neil S. Levy
*Attorney, Agent, or Firm*—Brian W. Dodson

[57] ABSTRACT

A method for releasing molecules (guest molecules) from the matrix formed by the structure of another molecule (host molecule) in a controllable manner has been invented. This method has many applications in science and industry. In addition, applications based on such molecular systems may revolutionize significant areas of medicine, in particular the treatment of cancer and of viral infection. Similar effects can also be obtained by controlled fragmentation of a source molecule, where the molecular fragments form the active principle.

12 Claims, 11 Drawing Sheets

Specified Stimulus

Becomes

CONTROLLED RELEASE OF MOLECULAR COMPONENTS OF DENDRIMER/BIOACTIVE COMPLEXES

This invention was made with Government support under Contract DE-AC04-94AL85000 awarded by the Department of Energy. The Government has certain rights in the invention.

BACKGROUND

This invention relates to the controlled release of chemical components trapped within confining molecular structures. More particularly, it relates to the resonant stimulation of selected bonds of the host molecular structure to either open an escape path for said chemical components, or to fragment said host molecular structure, resulting in release of said chemical components at a rate controlled by the intensity of the source of the resonant stimulation.

The general issue to be addressed by the present invention is the inefficient or inappropriate transport of molecular-scale agents in a wide variety of commercial fields, including but not limited to agriculture, various kinds of printing applications, medicine, and biotechnology. There are many examples of problems to be addressed relative to this general issue.

A very large-scale example which illustrates the general principles of the present invention concerns the safe transport and application of herbicides in agriculture. (This example applies to pesticides and a plethora of hazardous materials. Herbicides are simply one implementation used for purposes of discussion.) In concentrated form, nearly all herbicides are potent poisons to humans. This problem is now addressed by truck and/or rail transport of the herbicide itself to a wholesaler, storage there until sold, safe handling techniques by the user, and application to the fields. As a result, a great deal of the direct cost of using herbicides goes into elaborate safety precautions.

Despite precautions, however, a simple road accident can result in a hazardous waste spill of enormous significance, to the extent that most centers of population restrict the roads on which such transports can occur. Recent accidents involving major spillage of such materials have involved emergency evacuation or have had short-term health consequences for thousands of people. In addition, the long-term effects resulting from a single massive dose of most herbicides are essentially unknown. Accordingly, the need for great care (and the expenses associated with such care) is accepted in using such materials.

In one embodiment, the present invention would entrain the herbicide molecule as guest molecules in a complex, but essentially inert, host molecule. There is little or no covalent bonding interaction between the guest molecule and the host molecule. Confinement of the guest molecule within the host molecule is accomplished by design of a host molecule containing sterically-defined interior 'pockets', in which the guest molecules reside and are trapped essentially by the mechanical properties of the host molecule. Not only are the guest molecules trapped, but they are also insulated from interaction with the external environment.

How are such combined molecules applied to the herbicide problem outlined above? The product of the factory is now herbicide entrapped in an appropriate host molecule. The host molecule is designed to be stable against most chemical and environmental attacks. As a result, the product of the herbicide factory is orders of magnitude safer to transport, store, handle, and use than is the herbicide alone.

Given such effective confinement, how is the herbicide to be released from the host molecule and thus gain access to the fields on which it has been sprayed? Simply, the host molecule is designed so that exposure to strong sunlight alters the structure of the host molecule so that escape paths for the herbicide open. At least three simple approaches toward this goal exist. First, the strong sunlight can drive a volatile component from the host molecule, e.g., water. Given proper design, this will open escape paths for the herbicide. Second, photons from sunlight can directly interact with specific bonds of the host molecule, causing the steric structure of the host molecule to expand, thereby opening escape paths. Finally, exposure to the high near-UV intensity of sunlight can cause bonds of the host molecule to rupture, thereby immediately releasing the herbicide. The rates for any of the release processes will be a combination of the design of the host molecule and the intensity of the sunlight, so that specific release rates appropriate for the intended application are achieved.

What improvements in safety result from this type of guest molecule—host molecule structure? Direct exposure to the combined material involves greatly reduced risks. Given that the host molecule is designed so that it does not digest or dissolve in the blood stream, it will eventually be excreted by the body. As the body does not provide the environment needed to produce escape paths, the total dosage of herbicide absorbed should not occur on a physiologically significant scale. Such a compound system would thus reduce the dangers of transporting and using herbicides by orders of magnitude.

Confinement of herbicide as guest molecules in host molecules also greatly aids the cleanup of a spill. One aspect is that emergency workers need not take precautions as elaborate as are presently required, and can thus begin to control a spill sooner. Probably the major factor, however, is that exposure to strong sunlight is required to release any significant amount of the herbicide. If such release takes place by driving off water molecules, the spill can be misted with water to essentially halt all release of herbicide. If photon-chemical bond interactions are the key to opening the host molecules, the region of the spill can be fogged or simply covered with an inert tarp to prevent such exposure until the cleanup is complete. In general, trapping hazardous guest molecules in appropriate host molecules protects workers, the general populace, and the environment.

There are a host of new applications and improved techniques in medicine which are based on this invention. These include new avenues for chemotherapy, treatment of clots in blood vessels, treatment of benign prostatic enlargement, antiviral therapy, and many others. Details on these applications of the present invention will be given in the detailed description, but their common principle is to deliver the active drug inside an inert host molecule, or as a functional part of a fragmenting molecule, and trigger release of the drug at the therapeutic locality, most typically using optical or ionizing radiation. The advantage of such methods is that the local stimulus and release produces large doses of the active drug where it is needed. In addition, once the large local doses are distributed throughout the body by the conventional circulatory mechanisms, the total systemic doses may be very small, permitting larger concentrations of drug to be applied where it is effective while generating fewer systemic side effects.

Another field in which the guest molecule-host molecule structure offers many benefits is in various aspects of printing, including copying, high quality optical printing, and photography. The essence of this class of applications is to capture ink molecules inside a host molecule. In an electrostatic copier or printer, this material then replaces the fixer. The initial image is still recorded electrostatically on paper in the usual manner. The host molecules are then collected on the paper and held in place by this electrostatic field. When the paper is illuminated, the ink comprising the guest molecules is released from the host molecules. The small size of the ink (essentially isolated carbon atoms or small molecular chains) insures that the ink sticks indelibly to the paper without requiring a thermal fixing step as in conventional electrostatic printing. The copier/printing resolution can be greatly increased due to the essentially featureless distribution of host molecules while the overall process is simplified by elimination of the thermal fixing step.

A photographic process based on the present invention would operate in a similar manner to the above. A piece of paper or plastic film would be coated with host molecules containing guest molecules which act as ink. When the paper is exposed to light in a camera, the exposed host molecules open, producing a negative image. The resolution is improved over conventional film, as there is effectively no grain structure compared to the several micron grain structure of conventional high-resolution films. Color photographs could be taken by combining host molecules sensitive to a particular color with guest or fragmentation ink molecules producing that color.

No developing of the above negative is required, but a fixing step is needed to preserve the image against further exposure to light. One approach to solving this problem is to make the ink hydrophobic and the host molecule hydrophilic (or vice versa). The host molecules can then be dissolved from the surface using a polar solvent, leaving the ink behind in place.

For the foregoing reasons, there is a need for a technique for controlled release of guest molecules trapped in a host molecule where such trapping comprises steric forces or chemical bonds. A further need is for design of host molecules which can be expanded or fragmented by change of external conditions, in particular by optical or ionizing radiation. Such a technique would make possible a wide range of new applications, particularly in medicine, printing, and transport and use of hazardous materials.

SUMMARY

The present invention is directed to a method for controlled release of guest molecules from a host molecule, and to apparatus to carry out said new method, that satisfies the aforementioned needs of industry and medicine. A number of specific implementations of the above method, apparatus, and applications of said method and apparatus will be covered in the detailed description of the drawings and the claims. The common thread is the controlled release of guest molecules or molecular fragments from a host molecule upon manipulation of external conditions, most preferably by optical irradiation. Numerous embodiments and other features, aspects, and advantages of the present invention will become better understood with reference to the following descriptions and appended claims. No limitation to the invention beyond those listed in the claims is intended through the discussion of specific implementations.

DETAILED DESCRIPTION

In discussing host molecules, we shall concentrate on the application of dendrimers to this purpose. In so doing it is not intended to suggest that dendrimers are the only possible host molecules. For example, a similar function is served for some purposes by nanometer-scale micellar structures, and for others by $C_{60}$-type structures. However, dendrimers are presently the chemical structure of choice for application to the present invention. Discussion of this implementation is not intended to reject the possible utility of others.

Figure 1:
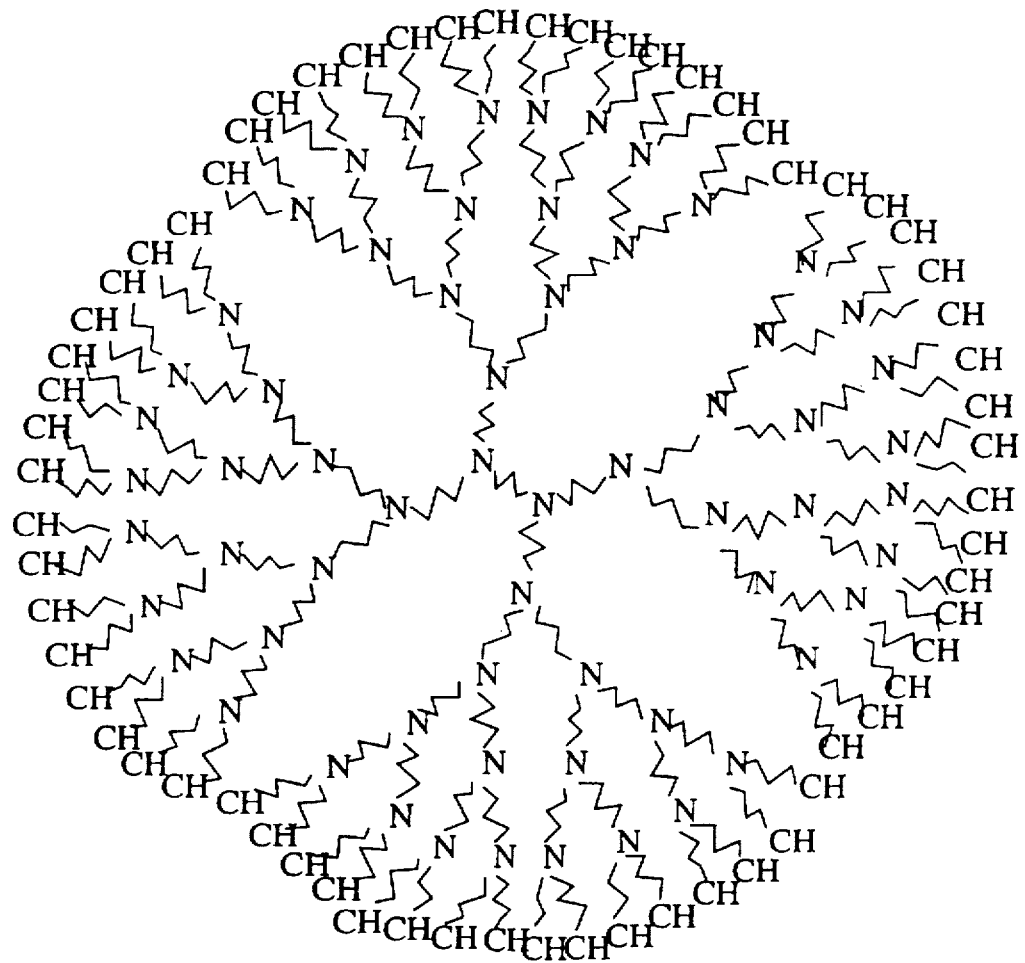
FIG. 1. A schematic dendrimer structure.

A dendrimer is a polymer or co-polymer comprising multiple branched chains attached at the bases, as illustrated schematically in FIG. 1. In this figure, three wedges attach in equivalent positions at a core molecule. Here the core molecule is described as symmetrical and the wedges as chemically equivalent, but neither feature is essential. Dendrimers are commonly synthesized by the simultaneous concentric growth of all branches from a common origin. (It is also possible to synthesize such dendrimers by a stepwise process in which one shell is added at a time.) However, better control over the final structure results from a recently introduced technique in which the wedges forming the dendrimer structure are synthesized separately and then are attached to a common core molecule. When the branches are grown simultaneously, growth continues until further additions are seriously impeded by steric hindrance. When the branches are pre-grown and assembled on a central core, steric constraints may inhibit the attachment of the individual branches to the core. However, controlled synthesis of a sub-maximal dendrimer is possible using this latter technique.

Figure 2:
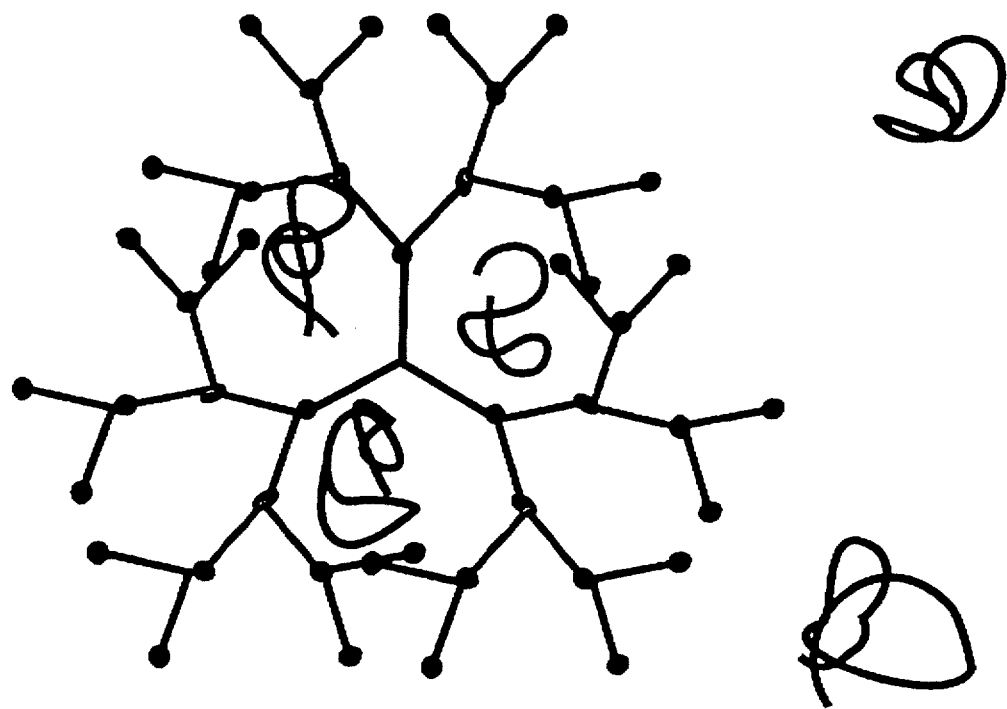
FIG. 2. Guest molecules entrapped in a schematic dendrimer structure.

The combination of steric hindrance and conformational constraints creates spaces within the structure of the dendrimer in which guest molecules can reside, held in place without chemical binding between the dendrimer and the guest molecule. (FIG. 2.) It is well known that some guest molecules can be introduced into said spaces by diffusion, usually with the aid of high pressure. Other forces, such as electrical attraction between polar regions of the dendrimer and the guest molecule can also be used for such introduction. It is also possible to synthesize the dendrimer in the presence of the guest molecule, thereby entrapping the guest molecule during the process of growth of the dendrimer.

Many distinct varieties of host molecules are possible. An example from nature is the protein coat of a virus, which contains the virus' DNA (or RNA) as a guest molecule. In the following, attention will focus on a particular subclass, the dendrimers. A dendrimer is a highly branched polymer, usually roughly spherical in shape, where the polymer chains are linked to a central core. If the branching rate increases faster than the surface area of the dendrimer as the dendrimer grows in size, steric hindrance between the densely packed branch ends at the surface eventually forces an overall structure having flexible internal cavities. Guest molecules, even those which do not undergo substantial chemical interaction with the dendrimer, can reside essentially permanently in these internal cavities. The packing at the dendrimer surface is so dense that diffusion of most guest molecules from the internal cavities is immeasurably slow. Accordingly, dendrimers form effective general-purpose containment vessels for a wide variety of guest molecules.

There are currently two approaches toward synthesis of dendrimers, which involve divergent and convergent synthetic processes. In the divergent techniques, subsequent shells of monomer units are attached, first to a core molecule, and later to exposed branch ends. The monomeric units contain a branch point, so that the density of branch end packing at the surface of the dendrimer increased with the diameter of the dendrimer. At some stage in the growth of the dendrimer, steric hindrance between branch units at the surface prevents the addition of another generation of branches. Growth of the dendrimer stops here (this is called sterically induced stoichometry). This process therefore produces dendrimers of nearly constant size, having a dense outer layer of polymer chain ends and sizable flexible internal cavities.

The convergent approach toward synthesis of dendrimers is to choose a chemical core molecule with N sites for attachment of polymer chains, grow N nominally symmetric wedges of highly branched polymer. These wedges are then assembled on the core molecule, resulting in a dendrimer having a very precise structure which again contains flexible internal cavities.

Synthesis of dendrimers produces a very effective host molecule for guest molecules. The confinement is so good that it is not obvious how to place the guest molecules in the internal cavities of the dendrimers. Two main techniques have been used previously for this purpose. The first is diffusion of the guest molecules into the dendrimer under pressure. Although a slow process, this works well for small guest molecules. The second approach is to synthesize the dendrimers in a solution containing the guest molecule as a constituent. As the guest molecule is chemically substantially inert with respect to the dendrimer, it does not participate in the dendrimer growth. However, as the dendrimer continues to grow and the internal cavities gain definition, a guest molecule can become mechanically trapped. This technique is perhaps of broader utility, but produces dendrimers having a rather broad distribution of guest molecule occupation. Note that when convergent synthetic processes are used, such techniques to trap guest molecules during assembly of the dendrimer are likely to be more easily controllable.

The above general techniques for synthesis and loading of dendrimers have dominated research on the topic since discovery of dendrimers a few years ago. At present, however, there is no controlled technique to release guest molecules which are trapped in the internal volumes of a dendrimer. There is also no controlled technique for fragmenting a large, inert dendrimer into small, active molecules. The current invention is intended to solve this problem.

Figure 3:
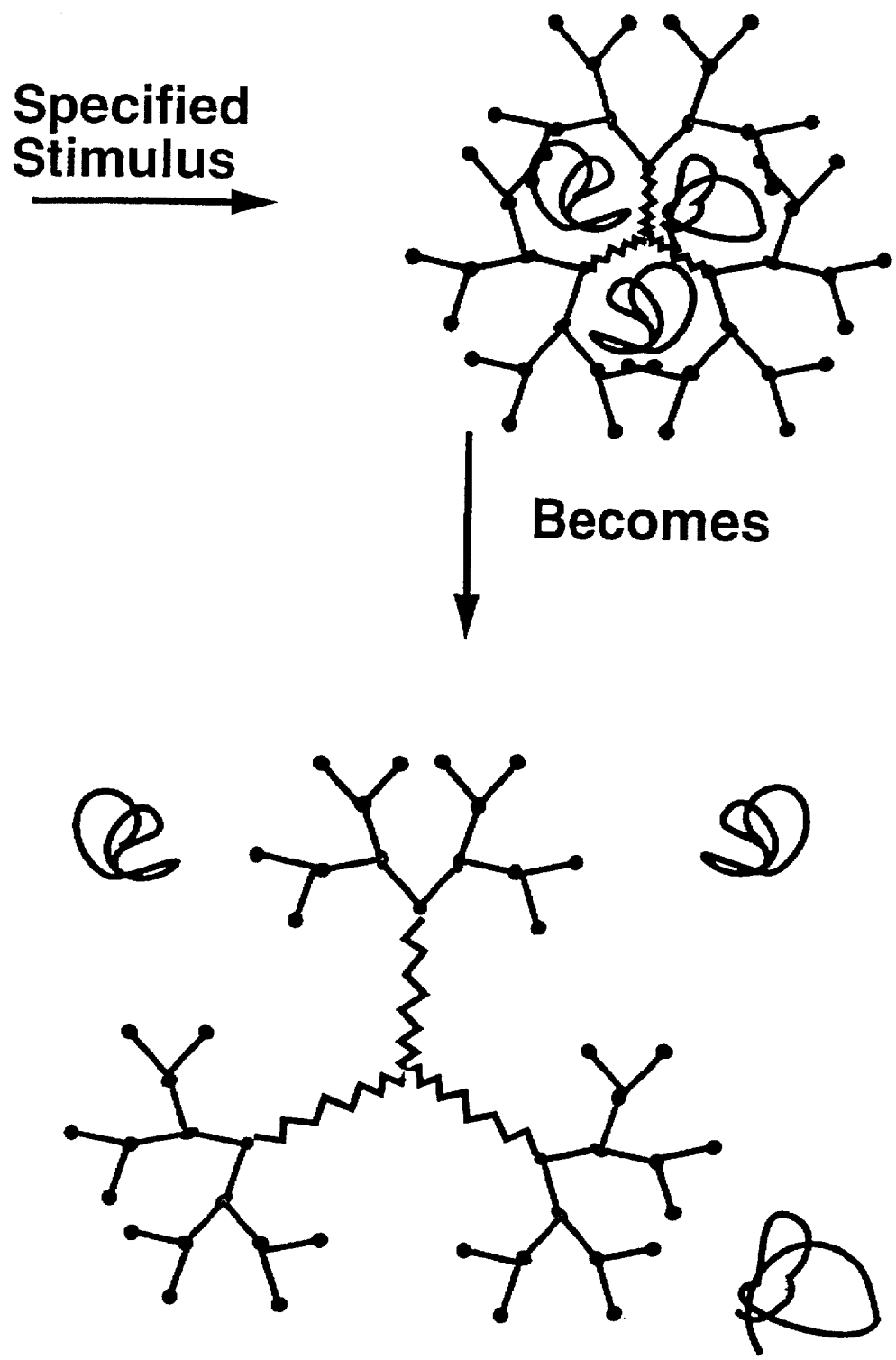
FIG. 3. Controlled release of guest molecules through induced expansion of the core bonds of a schematic dendrimer structure.

The invention is based on choosing a core molecule or other branch points having different properties than appear in current dendrimers. The simplest implementation for discussion is one where the core molecule or other branch points interact with incident photons. If the incident photons have energy equal to or greater than the resonant energy of the core molecule bonds, these bonds will undergo a transition into an excited state. Consequences of this excitation include increases in bond length, or transition into a non-bonding electronic configuration. The dendrimer diameter may increase, thereby relieving the steric forces at the surface of the dendrimer, and hence opening channels for escape of the guest molecules. (FIG. 3.)

Figure 4:
FIG. 4. Controlled release of guest molecules and release of the dendrimer wedges from the dendrimer core by rupture of the core bonds of a schematic dendrimer structure.
Figure 4:
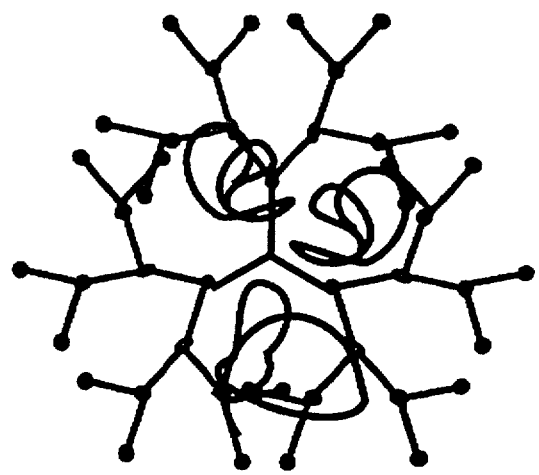
Figure 4:
Figure 4:
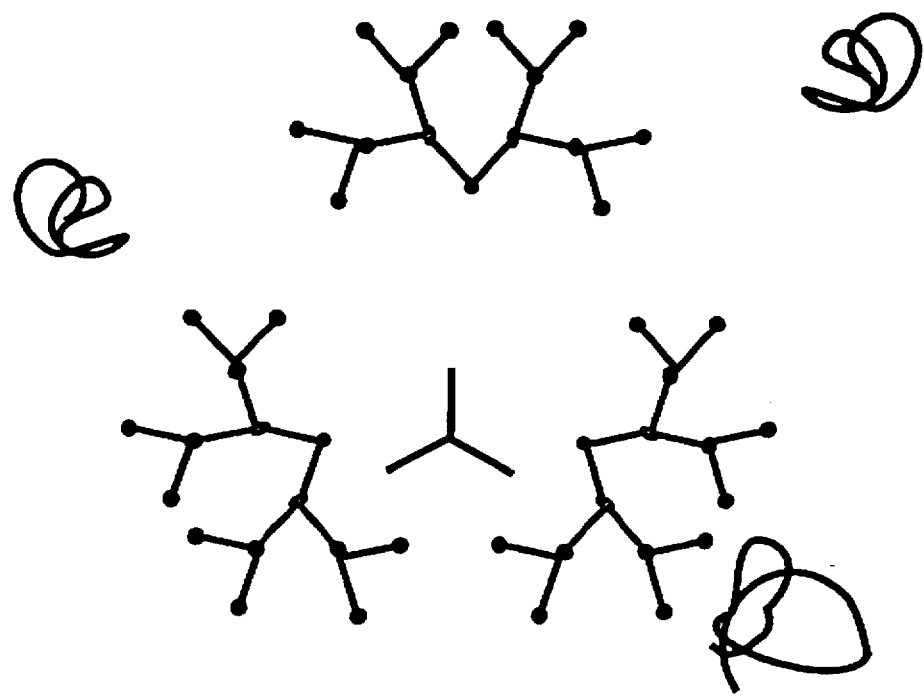

Another possibility is that the dendrimer fragments, breaking a core molecule bond or some other critical branch point releases one of the dendrimer wedges. The guest molecules can easily escape from the resulting structure. (FIG. 4.) Fragmentation can also be used to decompose all or part of the dendrimer into smaller reactive molecules, where said molecules are the active principle required for the desired application.

Our new invention can also be used in many cases to introduce guest molecules into the structure of an 'empty' dendrimer. One suspends the dendrimers in a highly concentrated solution of guest molecules in some mutually inert solvent. On optical irradiation of the dendrimer, the dendrimer stretches in a manner similar to that used to release guest molecules, opening channels to the interior cavities. The surrounding guest molecules rapidly diffuse into the internal cavities of the excited dendrimers. When the excitation of the core molecule dissipates, the dendrimer shuts again, but now contains a guest molecule.

Another aspect of this approach toward introduction of guest molecules into dendrimers is that the presence of a guest molecule will, through steric influence, alter the resonant energy of the core molecule bonds. Given proper design, it is thus possible for the excited dendrimer to act as a 'mousetrap', immediately falling out of resonance with the source of excitation and slamming shut when a guest molecule is in place. The presence of a guest molecule can also change the resonant frequency of the core molecular bonds sufficiently such that, once a guest molecule is in place, the core molecular bonds associated with that internal cavity will be non-resonant with respect to the excitation source. As a result, once an internal cavity is occupied, further optical irradiation at the original resonant frequency will not open that cavity, thereby trapping the guest molecule in place while still allowing guest molecules to be placed in other internal cavities of the same dendrimer. Such a loading procedure would be quite precise, but also should be rather more expensive than diffusion or trapping during dendrimer synthesis.

There are many methods of effecting reactions of the core molecule or dendritic branches, including heating, introduction of chemical energy (ionic or covalent reaction, changes in pH, enzymes, etc.), use of mechanical energy (including acoustic energy), optical and other radiant energy, and electricity or electric fields. The most favored methods for the present applications are heating and photo-irradiation exploiting thermally labile or photo-labile core molecules. The photo-irradiation method is facilitated by inclusion of chromophore functional groups in the core molecule.

Among the reactions considered for application are those that involve the breaking of bonds and those that involve isomerization or other rearrangement yielding modulation of the effective bond length. Some bond rupturing reactions include, but are not limited to, hydrolysis, photolysis, thermolysis, and electrolysis.

Many reactions suitable for the above purposes are well known in the chemical arts. Still, it may be useful to present a partial list of specific reactions here.

Specific bond-breaking reactions
1. Extrusion reactions (including ring contraction)—loss of $N_2$, CO, $CO_2$, $SO_2$, or other molecules.
2. Retro-Diels-Alder Ring Fragmentation.
3. Decomposition of Benzylic Alcohol Esters.
4. Decomposition of Allyl Esters.
5. Cleavage of Amine Oxides.

Specific bond rearrangement reactions
1. Electrocyclic ring opening and closing.
2. Cis-Trans isomerization.
3. Photo/Thermal isomerization of Spirobenzopyran based systems.
4. Isoimide to Imide isomerization.

The point is that there are a plethora of well-understood reactions on which core and branch point molecules having the desired expansion or fragmentation behaviors can be designed.

Another approach to the trapping and releasing of guest molecules is to use a host molecule which incorporates polyelectrolyte strands. Polyelectrolytes are polymers with ions bound to various portions along the length of the polymer. When the polyelectrolyte is in a bath containing a high density of counterions, the bound ions are shielded from each other, and the polymer takes on normal random configurations. However, when the polymer is in a bath with a smaller density of counter ions, the bound ions repel each other, and the polyelectrolyte takes on an extended configuration. Various methods of causing the polyelectrolyte to extend or collapse include: change of pH, change of solvent, change of temperature, and change of salt concentration in the surroundings.

Figure 5A:
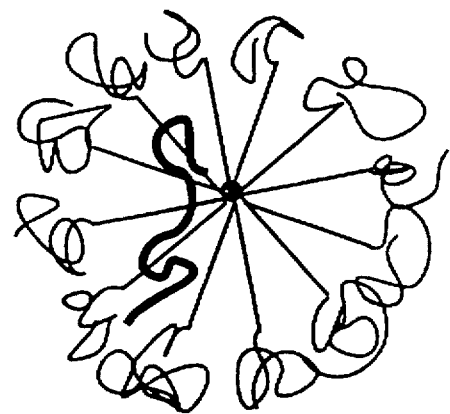
FIG. 5. A schematic star block-polyelectrolyte copolymer host molecule.
Figure 5B:
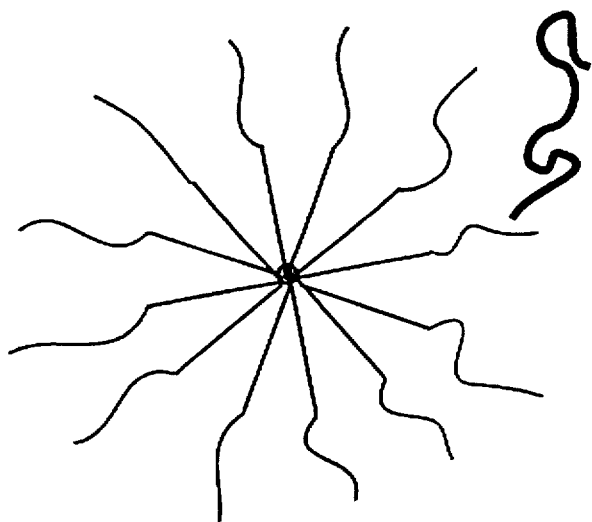

Two specific strategies for using polyelectrolytes for controlled release of guest molecules have been developed. The first involves the synthesis of a star block co-polymer having polyelectrolyte strands at the ends (FIG. 5). The star block structure of the interior of the host molecule provides room for guest molecules to reside. The guest molecules are trapped when external conditions are such that the polyelectrolyte strands take on normal polymer configurations (FIG. 5a). When the external conditions vary so that the screening of the ions on the polyelectrolyte is no longer effective, the outer shell of the host molecule opens, releasing the guest molecules (FIG. 5b).

Figure 6A:
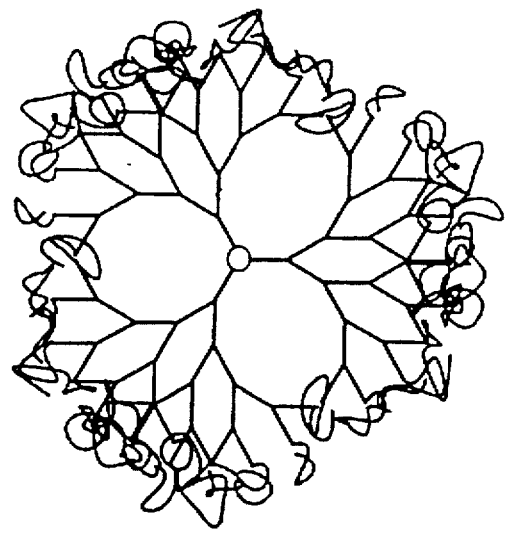
FIG. 6. A schematic fuzzy dendrimer host molecule.
Figure 6B:
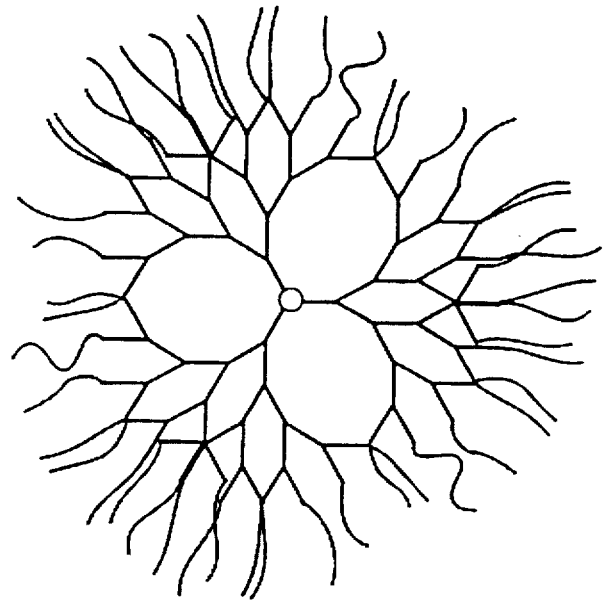

The second strategy uses what we have termed a fuzzy dendrimer. This is a low generation dendrimer with polyelectrolyte strands bonded to the surface of the dendrimer (FIG. 6). Again, the configurations taken on by the polyelectrolyte strands are determined by the local environment. When the environment shields the bound ions of the polyelectrolyte from each other, the polyelectrolyte contracts into clumps. Those clumps form a shell about the dendrimer, locking in guest molecules (FIG. 6a). A suitable change in environment, such as a change in pH or an increase in temperature will cause the polyelectrolyte segments to take on extended configurations, thereby opening the outer shell of the fuzzy dendrimer and allowing passage of the guest molecules (FIG. 6b).

Many other possible structures for host molecules and for fragmenting molecules exist, e.g., fragmentable polymerized micelles. Those discussed in detail are intended as examples, and not to limit the scope of the present invention.

Demonstration

We have demonstrated the practicality of controlled release of guest molecules from a dendrimer through application of UV radiation. The molecule chosen is a first order dendrimer with a core molecule designed to fragment on exposure to UV light. Although the structure of a first order dendrimer is not sufficiently developed to trap guest molecules, the emphasis here is that the fragmentation which would lead to release of mechanically trapped guest molecules is demonstrated. Such fragmentation also demonstrates the principle of complete fragmentation of a dendrimer into smaller active molecules.

Figure 7:
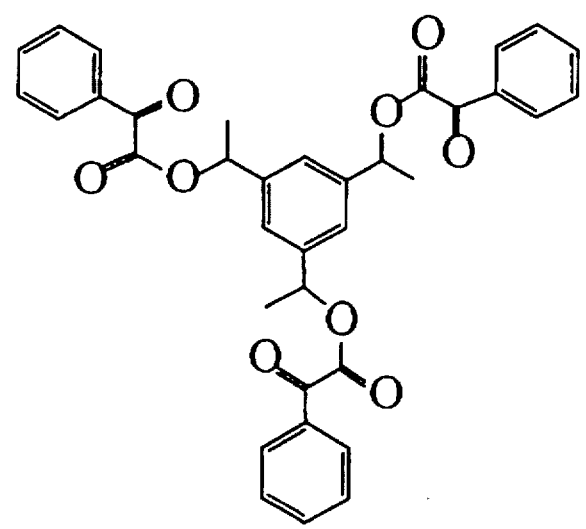
FIG. 7. A model fragmenting dendrimer synthesized by the inventors.

The model molecule is an aromatic triketoester (ATKE) whose structure is shown in FIG. 7. The core molecule is trimethyl-1,3,5-benzenetrimethanol, which is bonded to the branching chain ends to form a ketoester. When subjected to UV radiation, the polar C—O bonds between the core molecule and the dendrimer branches break, yielding triacetylbenzene, benzaldehyde, and CO as fragmentation products.

Approximately one gram of ATKE was synthesized through the following process:

1) Commercially available (Aldrich Chemical Company) 1,3,5-triacetylbenzene was reduced with $NaBH_4$ in good yield to give $\alpha$, $\alpha'$, $\alpha''$-trimethyl-1,3,5-benzenetrimethanol (Compound A);
2) Commercially available $\alpha,\alpha$-dichloromethylmethyl ether and benzoylformic acid were reacted to produce in good yield benzoylformic acid chloride (Compound B);
3) Compounds A and B were mixed in a 1:3 ratio and allowed to react, thereby producing the compound referred to as ATKE in good yield;
4) The ATKE was purified in a process comprising column chromatography, and;
5) $^1H$ and $^{13}C$ NMR spectra were taken, confirming the structure of ATKE.

Fragmentation of ATKE when exposed to UV light was then demonstrated in the following experiment:

1) A small sample of ATKE was removed, and an NMR base line spectrum recorded;
2) The ATKE sample was subjected to 254 nm wavelength UV light for nine hours, with periodic examination by NMR spectroscopy, and;
3) Progressive changes in the NMR spectra were compared to determine the chemical changes taking place during optical irradiation.

Figure 8:
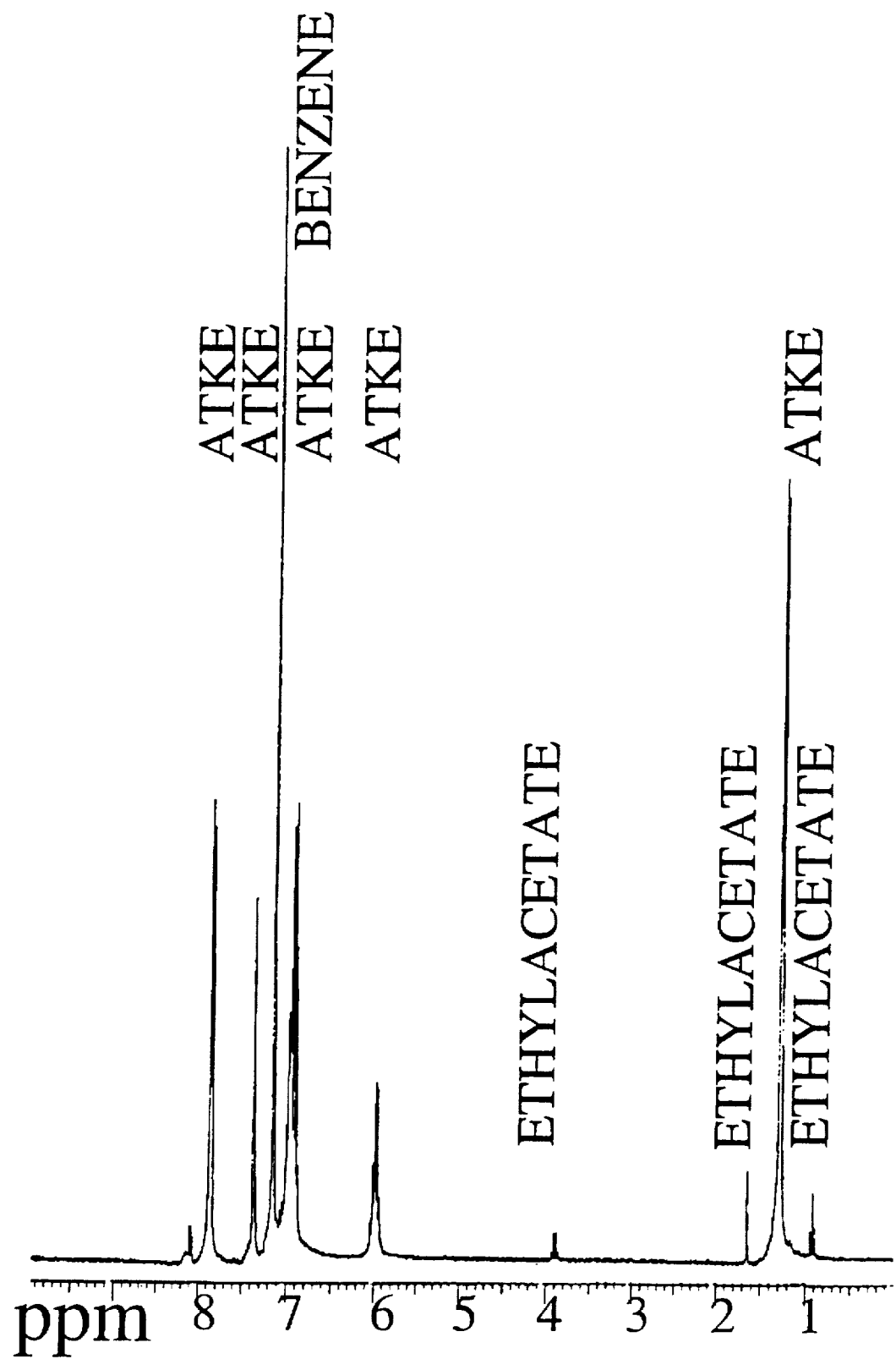
FIG. 8. Baseline NMR spectrum of a benzene solution of the model fragmenting dendrimer.

FIG. 8 shows the NMR spectrum before exposure of the sample to UV light. ATKE is seen as well as benzene and ethylacetate, which are impurities in the system. (The benzene forms a small component of the 99.5% deuterated benzene used as solvent for the material, and the ethylacetate is an artifact of the purification process.)

Figure 9:
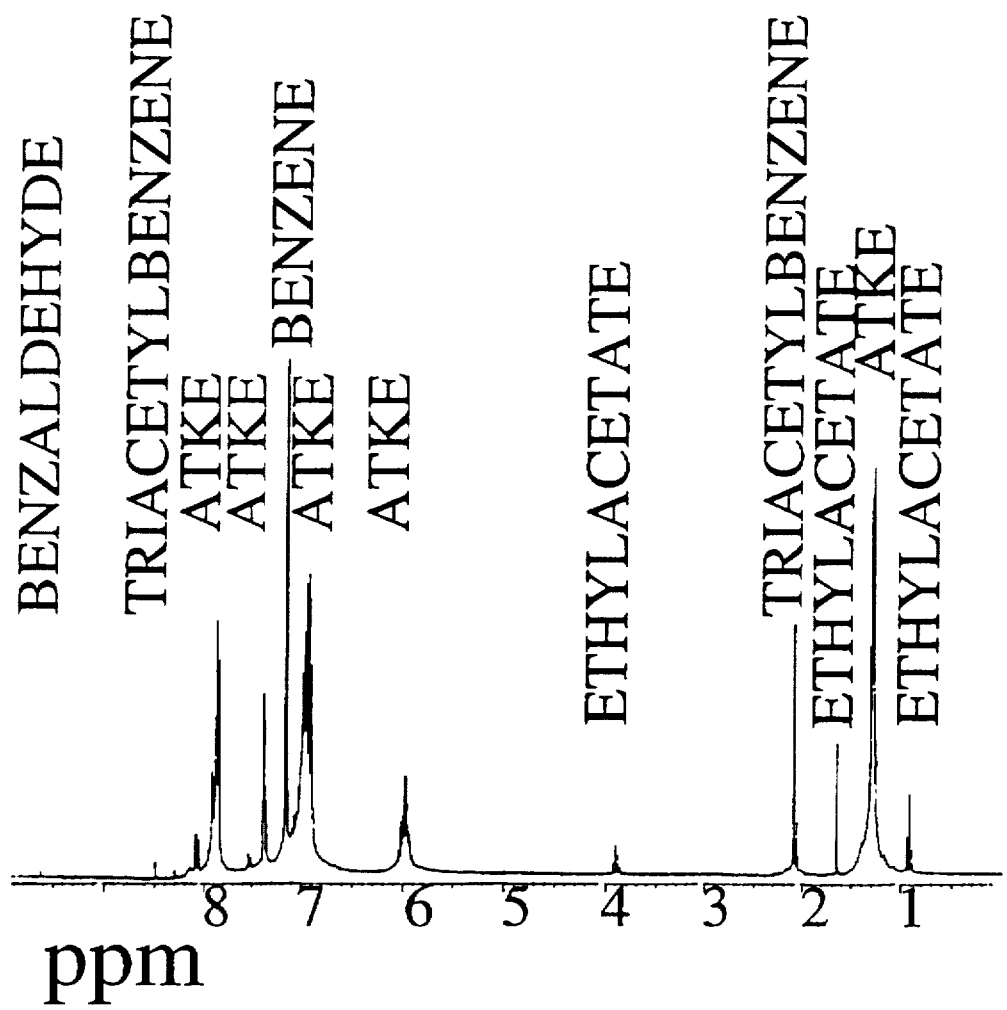
FIG. 9. NMR spectrum of a benzene solution of the model fragmenting dendrimer following 60 minutes exposure to a given intensity of UV light.

FIG. 9 shows the NMR spectrum of the ATKE solution after 60 minutes of exposure to UV light. (All NMR results are normalized to a constant amount of ethylacetate, which is stable under UV irradiation.) The ATKE resonance has been substantially reduced, and there are two new resonances associated with the fragmentation products benzaldehyde and triacetylbenzene.

Figure 10:
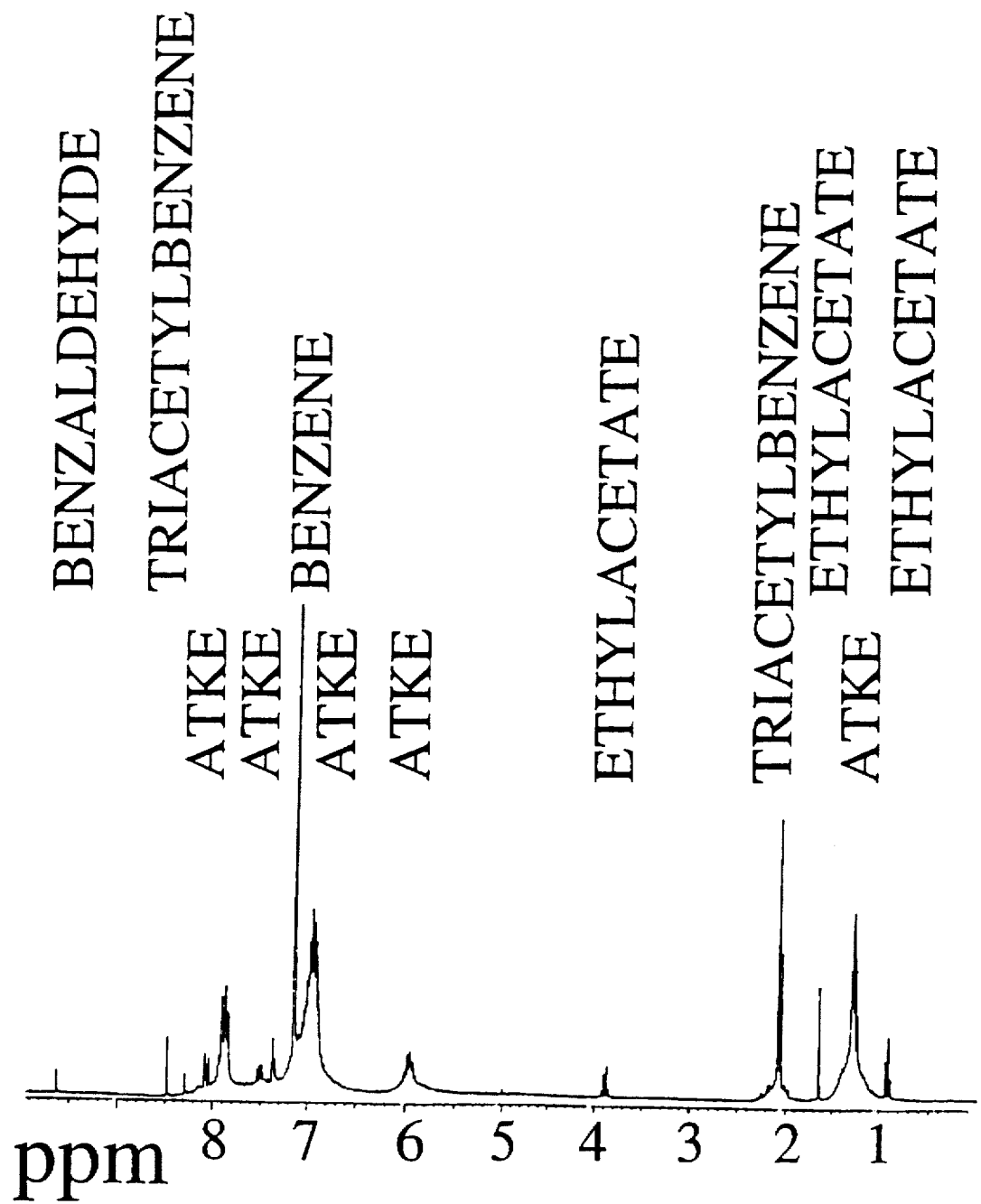
FIG. 10. NMR spectrum of a benzene solution of the model fragmenting dendrimer following 180 minutes exposure to a given intensity of UV light.
Figure 11:
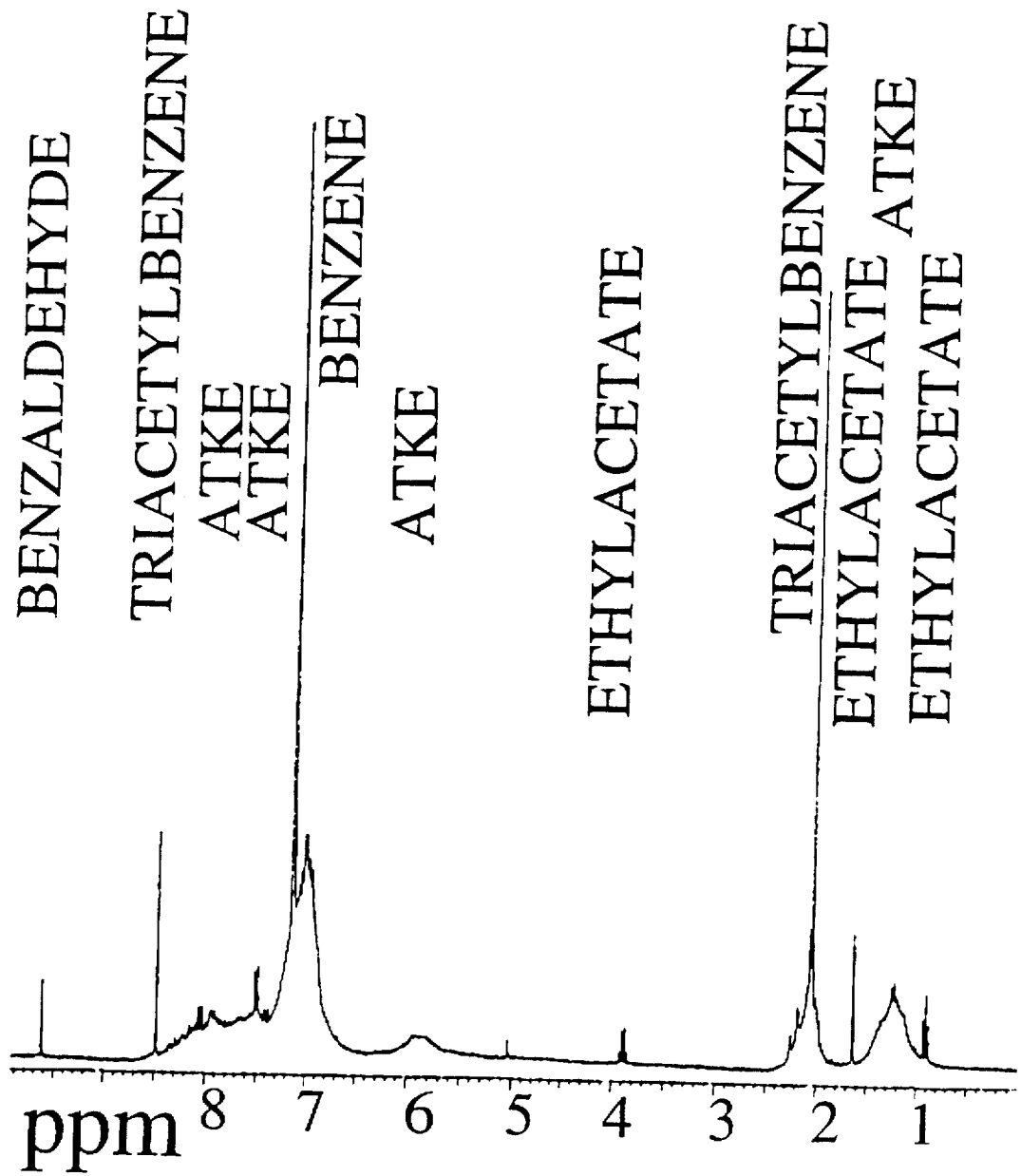
FIG. 11. NMR spectrum of a benzene solution of the model fragmenting dendrimer following 540 minutes exposure to a given intensity of UV light.

FIGS. 10 and 11 show the NMR spectra after 180 minutes and 540 minutes of exposure to UV light, respectively. By 540 minutes most of the original ATKE has been fragmented by the UV light and the resonances of the reaction products have become a substantial part of the NMR spectrum. It is interesting to note that partially fragmented products do not appear in detectable quantity. This suggests the UV excitation of the ATKE is sufficient that all the C—O bonds connecting the dendrimer chains to the core molecule break, and that no other bonds seem to be affected. This, of course, is the ideal situation for the present invention.

The same experiment was also carried out using tetrahydrofuran as the solvent rather than benzene. In contrast to the case of benzene, tetrahydrofuran is highly polar, and thus the UV excitation of the dendrimer is provided with a channel for deexcitation distinct from the fragmentation reaction. Despite this, effective fragmentation under UV irradiation was observed. This suggests that electromagnetic interaction with the surrounding molecules is unlikely to alter significantly the basic fragmentation process. The generality of such fragmentation processes is thus established, and predictive design of appropriate molecules for fragmentation is within the current state of the art.

Applications

The containment of active guest molecules within host molecules, the related technique of fragmentation of a molecule into smaller active molecules, and techniques for the controlled release of the active molecules have an extremely wide range of application. The application of the present invention to the handling of hazardous materials was described thoroughly in the background section.

Another example of the benefits of the present invention for the handling of hazardous materials appears in the field of aviation. Jet fuels exist which are much more energetic than those presently used in commercial and military applications. Unfortunately, such fuels are quite unstable, and thus have been considered too hazardous for application. It is possible, however, to insulate such fuel molecules from the external environment in a manner analogous to that described earlier for herbicides. When the jet fuel is confined by steric hindrances within a relatively inert host molecule, two effects will be seen. First, the rate of reaction of the jet fuel will fall precipitously. This is true even if the jet fuel is so unstable that it can be used as a monopropellant. Second, as the individual molecules of jet fuel are 'insulated' from each other, the excitation resulting from reaction of an individual molecule will dissipate into inert material before triggering reaction in another jet fuel molecule. This prevents energetic chain reactions of the jet fuel, so that the instability of the jet fuel is greatly reduced.

It may appear that the energy density of the jet fuel is also reduced, because of the presence of the relatively inert host molecules. This, however, need not be true. For purposes of stabilization the host molecule need only be more stable than the jet fuel. If the jet fuel-host molecule is designed as a system, the ultimate energy density can be similar to the most energetic jet fuels known today. If the guest molecules (jet fuel) are released by expansion (relief of steric hindrances), they are then free to react not only with each other, but also with the host molecules, which may add energy to the overall reaction by serving as an additional source of fuel or oxidizer. Another technique is to release the jet fuel molecules by fragmentation of the host molecule. If the host molecule is designed to be inert relative reaction with the jet fuel molecules when intact, but so that the fragmentation products react strongly with the jet fuel molecules, it is possible to increase the energy density of the combined system. An example is when fragmentation of the host molecule makes fluorine atoms available for bonding. As the HF bond has the highest energy per bonding electron, enabling such reactions should produce extremely high energy densities.

In summary, there are two classes of application of the present invention to stabilization of high energy density jet fuels. The first is to contain known high energy density jet fuels as guest molecules in a relatively inert host molecule. The second is to design a system of guest molecules and host molecules in which, upon release of the guest molecules by expansion or fragmentation of the host molecule, the host molecule or the smaller reactive fragments produced on fragmentation take part in the overall reaction of the jet fuel.

Applications of the guest molecule-host molecule structure in the medical field are widespread and potentially of extreme importance. Note that all of the applications to be discussed can also be accomplished using fragmentation of the host molecule to release the guest molecule, or by fragmenting a large inert molecule, such as a dendrimer, into smaller active components.

We begin by discussing the treatment of cancer by drugs, or chemotherapy. Chemotherapy is one of the primary tools medical science currently has against cancer. However, if possible an invasive technique (surgical removal) is generally chosen as the first mode of attack, followed by a combination of chemotherapy and radiation treatment when appropriate. Chemotherapy is usually considered as the primary treatment modality only when the tumors are widespread or inoperable. The reason for this is that there is little fundamental difference between tumor tissue and healthy tissue at the cellular level. As a result, most chemotherapy agents are chemicals which show marginally greater lethality to tumor tissue than to the patient, the hope being that tumor growth can be negatively impacted without poisoning the patient too seriously from the general systemic effects of the chemotherapy agent. This is a delicate balance, and hence is generally used in concert with or as a follow-up to other, more targeted therapies.

Entrapping the chemotherapy agent inside a host molecule, or producing the chemotherapy agent in situ by fragmentation of a large, essentially inert molecule, offers a rare chance to improve effectiveness of the existing chemotherapy agents, and to produce a whole new class of highly effective agents. The chemotherapy agent is trapped in a host molecule which is inert to bodily fluids. The combined structure is then injected into the patient. The confined agent distributes itself innocuously throughout the body, with at most a very slow diffusion of the agent from the host molecule. If the active chemotherapy agent is produced by fragmentation of a larger molecule, there will be essentially no losses to diffusion. In one implementation, such structures may be designed where the chemotherapy agent forms the wedges in a dendrimer structure, being bonded to a core molecule. When external excitation fragments the core-wedge bonds, the active agent is released. Such structures are unlikely to be totally inert in the body, but will have greatly reduced reactivity relative to the chemotherapy agent itself.

Appropriate radiation is then applied to the tumor. This may be external UV light for tumors near the skin. UV light fed through catheters using fiber-optic light guides, ionizing radiation from radioactive implants or external generators, and other possibilities currently known in the art. Given that the host molecule is sensitive to the radiation, however, it will either expand or fragment, thereby releasing the chemotherapy agent precisely where it is needed. (Note that when ionizing radiation is used for this purpose, the tumor is simultaneously exposed to chemotherapy and radiation treatment.)

The highly targeted nature of this type of chemotherapy gives enormous leverage for the treatment of isolated tumors. Systemic circulation distributes the released chemotherapy agent around the body. However, the systemic dose to the body as a whole outside the immediate region of irradiation is much lower than that to the tumor itself, because effective densities of active agent only exist in the immediate vicinity of the tumor. As a result, the therapeutic window between killing the tumor and killing the patient is much broader, meaning that higher doses can be safely delivered to the tumor in normal practice.

The precision of the spatial targeting of the chemotherapy agent, and the resulting low systemic doses, should provide a large enough difference between systemic and tumor dosage that it becomes possible to consider active agents which show no particular specificity for tumors, or which are much too poisonous for conventional application. The specificity of application is provided by the local irradiation of host molecules, thereby allowing agents with one or more serious side effects to be used. This application of the present invention offers the potential of revolutionizing treatment of broad classes of cancers.

There are other diseases and conditions in which targeted delivery of a therapeutic agent to a particular bodily region is of benefit. Almost any treatment which now involves a systemic dose of a therapeutic agent to the body in order to reach a localized region of the body, said systemic dose being large enough to produce undesired (and perhaps unacceptable) side effects, could benefit through targeted delivery systems similar to that described above for cancer treatment.

It is also possible to replace numerous surgical techniques with techniques based on the current invention. An example is the treatment of benign prostatic hyperplasia, which is the enlargement of the prostate commonly found in middleaged and elderly men. When the enlargement is sufficient to cause urinary tract obstruction, a surgical procedure called transurethral resection is the usual mode of treatment. The success rate for removing the obstruction is very high, but other treatment modalities are actively being searched for.

The application of the current invention would be to inject the patient with a host molecule harboring lysitic molecules which induce tissue lysis through any of a number of mechanisms. One implementation would then be to thread a fiber-optic probe to the constricted region of the urethra, and irradiate a very small region with UV light (or other radiation) which releases the lysitic molecules, thereby producing local atrophy of the prostatic tissue while causing minimal damage in regions distant from the blockage itself. The guest molecules not so released are excreted rapidly from the system, still protected by the dense unreactive surface of the host molecule. Such an approach may result in fewer side effects than the surgical removal of tissue.

Another condition which is amenable to a procedure of the above type is circulatory thrombosis and embolism, including the proximate cause of heart attacks. Thrombosis is a condition where there are clots in the circulatory system attached to the walls of the blood vessels; such a clot becomes an embolism when it breaks free to become lodged somewhere else in the circulatory system. At present, emergency conditions involving obstruction of circulation due to thrombosis or embolism are usually treated surgically (perhaps in combination with clot-dissolving drugs, such as heparin), whereas the treatment of non-emergency cases usually focuses on systemic injection of anticoagulant and clot-dissolving drugs. As surgical intervention is always dangerous in itself, alternatives would be welcome. However, the systemic use of anticoagulants and clot-dissolving drugs is also dangerous, as the possible of triggering uncontrolled bleeding is always possible. Finally, the most effective clot-dissolving drugs currently available, such as TPA, are genetically engineered, and are extremely expensive in systemically effective doses. As a result, treatment of such conditions, when serious, is always expensive in hospital time and drug cost as well as in inherent risks.

Using the present invention, however, significant improvements on the present treatment modality can be made. The general technique is the same. A systemic dose of host molecules harboring anticoagulant or clot-dissolving drugs would be injected. Being confined, these have no systemic effect on the body. A fiber-optic catheter would be threaded to the site of the clot, and oriented so that the emerging radiation shines on the region of the clot. The radiation releases the active drugs in the immediate vicinity of the clot, bathing the clot in a much higher dose than can safely be applied to the entire circulatory system. The final state, once the clot has been dissolved, is that there is a small systemic dose of anticoagulant which continues to act on the clot, but which is much less dangerous than a systemic dose which would have produced equivalent doses to the clot in the early stages of treatment. Note that if a blood vessel is completely blocked, this treatment will be much less effective, as blood flow will not efficiently bring fresh confined drug into the vicinity of the clot to be released. This can be countered by injecting the host molecules at the site of the clot, e.g., through a catheter (perhaps the same one used for irradiation). Also, in extrema (massive heart attack or pulmonary emboli) surgery may still be the treatment of choice. However, in many cases, the procedure outlined provides the desired dissolution of clots with greater safety, shorter hospital stays, and smaller drug costs.

Having explained the general principles involved in applying the present invention to the treatment of localized medical conditions through the above implementations, numerous additional examples will be clear to one skilled in the medical arts. There are, however, at least two more classes of applications to which this invention may be applied. The first is optically-controlled biofeedback treatment, and the second is antiviral therapy.

There are many diseases whose source is a disruption in the normal chemical or electrical functioning of the body. An example is epilepsy, in which a local instability in the electrical functioning of the brain grows to cover an appreciable portion of the brain, whereupon any of a wide variety of disabling and disturbing symptoms take place. The present invention can be applied to a new treatment for epilepsy.

The new epilepsy treatment is suited for cases in which a focal source of epileptic instability is located, but surgical removal is either not appropriate or not chosen by the doctor and patient. The patient will take, on a regular basis, a host molecule containing therapeutic guest molecules. In this case a fast-acting benzodiazepine, such as triazolam, or a fast-acting barbiturate, such as hexobarbitol, which are used in the treatment of status epilepticus, would be preferred guest molecules, although many other possibilities will be apparent to one skilled in the treatment of epilepsy. The host molecule will be designed to release the guest molecules on exposure to an intense source of UV light. The sensitivity of the host molecule must be adjusted so that the amount of active drug which escapes on systemic exposure to direct sunlight is clinically insignificant.

A fiber-optic is threaded through blood vessels to the focal site of the epileptic seizures. EEG monitoring of this region of the brain is provided in a preferred embodiment by electrodes carried on the fiber-optic, or otherwise by EEG information implanted separately or determined from scalp electrodes. When changes in the EEG appear which suggest the onset of an epileptic incident, light of the appropriate wavelength to release the guest drug molecules from the host molecules is sent through the fiber-optic. As the focal area of the oncoming epileptic seizure is flooded with the drug molecules, the focal activity ceases, and optical irradiation of the area stops (perhaps after a period of time in obdurate cases). The control of drug dosage and duration is controlled by feedback information from the EEG signatures of the focal site.

The above approach toward control of epileptic seizures is particularly appropriate for the control of previously uncontrollable seizures, because a huge dose of a sedative and antiseizure drug can be released precisely at the focal site exactly when such treatment can still stop a general seizure from developing. It is an invasive technique, as the fiber optic has to pass into the blood vessels of the brain. Although it does not penetrate the blood-brain barrier, there is still a danger of infection. This danger, however, is markedly less than in treatment systems proposed which replace the fiber optic with a hollow microcatheter through which an appropriate drug is pumped when abnormal EEG signs are detected, because nothing must pass through the catheter except light. Our technique is also likely to result in considerably less cognitive and motor function disturbance than does a typical surgical treatment for epilepsy, in which a substantial region of the brain is usually removed, or major nerve bundles are severed.

A variation of the above technique for treatment of epilepsy is to permanently implant a light source capable of activating the drug precursor material, whether through expansion or fragmentation. If the light source is powered inductively, there need be no break in the skin, and the possibility of infection is greatly reduced. The remainder of the EEG biofeedback control of epilepsy operates in the same manner as above, save that the EEG electrodes are likely to be inactive when the inductive power source operates because of interference. A pulsed mode where drug delivery alternates with EEG measurements on a time scale of several seconds is most likely to avoid interference problems while still minimizing the dosage applied to the focal area to stop the oncoming seizure.

Additional applications of the present invention appear in the field of antiviral chemotherapy. This field is at best in an infancy which is governed by no general model. The few currently approved antiviral compounds were all discovered by random biological testing in the laboratory. In addition, the range of usefulness of any one antiviral compound is very small, e.g., antiherpes compounds have no effect against influenza. There is thus a huge open field for development of effective, broad-spectrum antiviral compounds.

Antiviral drugs function by inhibiting virus-directed processes while allowing normal cellular functions to proceed. The most effective drugs to date act by inhibition of viral nucleic acid synthesis, or by preventing either the adsorption or escape of the virus from a cell. Such approaches are extremely specific in action, both as to the virus inhibited and the cells under attack.

In general, antiviral drug therapy is aimed at either preventing a virus from entering the cell, preventing the virus from taking over the cell metabolism, or slowing the escape of replicated virus from an infected cell. None of these approaches actually aim at inactivating the virus, but rather at slowing progress of the disease to the point where the patient's immune system can handle the infection. (This is one reason that drug treatment of HIV infection is not very successful, as HIV infection seriously compromises the patient's immune system.)

An approach to antiviral therapy which has potential for broad-spectrum effectiveness is to bind a lethal drug molecule directly to the virus itself. The object here is to inactivate free virus (and possibly some latent viruses) before cell entry so that replication cannot occur. Ideally, one would construct the drug so that the virus binds to it as it would to a cell. All viruses have on their surfaces a protein containing a receptor-binding site that reacts specifically with a corresponding receptor on a cell surface. This precise key and lock interaction explains why most viruses are restricted to certain tissues within a very small range of host species.

The cellular receptors are glycoproteins or glycolipids having specific chemical structure and steric environments. In principle one can create a 'cell substitute' molecule which would simply block the viral receptor-binding sites by simulating the receptor structure of the cells at risk for infection. The viruses are then inactivated, as they cannot bind to the cell surface. Such techniques are useful, but viruses can still enter a cell by viropexis, a process in which the cell forms a microvacuole of the external fluid at its surface (this is a normal function of cells, which allows them to sample and react to the external environment). If the sample of external fluid includes a blocked virus, the cell is infected, as the binding site block will not prevent the operation of the virus within the environment of the cellular metabolic processes. Accordingly, finding an active drug to use as a cell substitute may be more effective.

Many requirements must be satisfied in order to make such an active cell substitute, however. Clearly, the cell substitute must exhibit an appropriate receptor structure to mimic the class of cells at risk. The cell substitute must also produce minimal systemic effects, as the density of cell substitute will have to be quite large (very roughly on the order of 100 μg/ml) to insure that the majority of the viruses targeted interact with the cell substitute, rather than the cells themselves. Despite this systemic inactivity, the drug on which the cell substitute is based must be so powerful that a few molecules can inactivate a virus.

The most likely entity of which a few molecules would be capable of inactivating a virus is a catalytic agent of some form. Most viruses are covered by a lipid-rich outer coat which forms the envelope of the virus. Such viruses include the herpesviruses, the retroviruses (including HIV-1 and -2), and influenza. Those that are not so coated present a surface comprising protein molecules, generally in a multifaceted structure having some symmetry. This class includes the hepatitis viruses and the common cold viruses. In either case, catalytic agents are known in the art which can cause simple and cross-linked polymerization between the surface molecules of a virus. Given enough such damage, a virus is permanently inactivated.

To achieve the total functionality required to effectively inactivate viruses using a single drug molecule is a difficult task. At the same time, the drug molecule must be a free-radical catalyst (or something similar in function), inert to body tissues and fluids, and which possesses a receptor simulating that of the body tissues at risk. The difficulty of this task perhaps helps to explain the lack of effective antiviral therapies based on the above approach.

Such antiviral therapies, however, can be developed based on the present invention. Briefly, the drug molecule, which in one implementation acts through catalyzing polymerization of the virus surface layer, would be the guest molecule in a host molecule. The host molecule should be designed to contain as many guest molecules as possible. (This may in some cases be more effectively accomplished when the active drug molecules are fragmentation products of a larger molecule.) Finally, molecules which simulate the cell receptor sites are bonded to the surface of the host molecule. (An alternate possibility is that the host molecule itself may be designed to have the proper receptor structure.) This composite structure then forms the antiviral drug.

In our invention, each of the required functions of an inactivating antiviral drug is separated and expressed on three different molecules, making each molecule easier to design. As assembly of the total molecular structure is straightforward, obtaining a composite antiviral drug is a practical proposition. Once the antiviral drug is introduced into the system and given time to interact with the free virus having the appropriate receptor-binding sites, optical or ionizing radiation is used to release the guest molecules, which then inactivate the virus.

In addition, one may obtain antiviral drugs for various species of virus by assembling appropriate combinations of guest, host, and receptor molecules from a 'parts kit'. If a given virus has an envelope, one chooses a guest molecule which polymerizes lipid envelopes. If not, a guest molecule is chosen which polymerizes protein coats. An appropriate host molecule is chosen to contain the guest molecule and release it when the proper conditions are applied. Finally, a cell receptor mimic is chosen to simulate the identity of the tissue at risk. A wide range of antiviral agents having activity against specific viruses can thus be assembled from a combination of three components, each chosen from a rather small set of possibilities.

Another application of the present invention is to controlled release of hormones and related bioactive substances for a variety of bodily control functions. A nearly constant rate of release can be obtained through proper design of a guest molecule-host molecule structure, where the guest molecule is a hormone and the host molecule simply acts as a carrier. Alternately, a molecular structure can be synthesized so that fragmentation produces the desired hormones.

In either case a constant rate of release of hormones and related bioactive substances can be obtained. Such structures thus offer great promise for application to time-release drug formulations and to transdermal patches for application of drug materials. As conventional approaches to these applications yield a dosage rate which falls off with time, use of the present invention would improve the constancy of the dosage rate.

Some detail has been presented of several new applications of the present invention to medical therapy. Applications to this field are not meant to be restricted to those implementations described, as many other possibilities will be clear to one skilled in the medical arts. The only restrictions intended are those appearing in the claims.

Application of the present invention to various aspects of the printing arts was discussed in the Background section.

We now turn to a range of common products in which new approaches to controlled release would improve the desired function. In particular, the use of cosmetic and related products such as perfumes and deodorants would benefit greatly by using the controlled release techniques of our invention. The principle is the same, that the active molecule is trapped in an inert carrier which opens and releases the active agent upon the proper change of external conditions.

One difference between the most expensive perfumes and their less costly imitators is the length of time that the fragrance lingers. Even if the scent is accurately replicated, at present it is not possible to produce a long-lingering and yet subtle perfume without using natural products which are extremely expensive and whose sources are threatened by various environmental and species protection acts.

The application of our invention to this problem is to provide controlled release of less expensive substitutes for the premier perfumes by containing the scents in host molecules from which they are gradually released, allowing the scent to mimic the desired lingering quality. Fragmentation of molecules to produce molecular fragments having the desired aromatic propeerties is also possible to induce.

This function in itself might be accomplished by designing a host molecule through which the active elements of the perfume could slowly diffuse under ordinary conditions. This, however, is a non-optimal solution, as the intensity of scent would reduce with time faster than an active release mechanism would allow. Also, perfume would be released when not desired. In particular, the product would have a short shelf life. Accordingly, an actively triggered release of the scent from the host molecule is desired.

Many aspects of the skin microenvironment change with external conditions, activity, and emotional state. The most obvious example is sweating from exercise, but a flush, which affects both skin temperature and pH values, often results from a sudden change in emotion. Coupling such changes in the skin microenvironment with the opening mechanism for the host molecule would offer the benefit of providing increased amounts of perfume when the user is experiencing suitable environmental conditions (e.g., getting wet in the rain) or internal emotional states (e.g., excitement).

The mode of action of such specific host molecules would best depend on chemical environment, so their action is independent of e.g., light levels. Several suitable reactions were listed earlier in the discussion on how to release guest molecules from dendrimers.

Application of the present invention to controlled release of deodorants presents the same general problems as those involving perfumes. One simplification is that the primary release trigger can be sweat, or sweat-associated changes in skin pH, which makes design of a suitable host molecule a rather straightforward process. One problem, however, with deodorants is that the present deodorants may not be entirely suitable for use in molecular dispersions. While release of a fragrance is straightforward, to produce a drying effect may be difficult, as absorbent materials generally work in part because of a porous microscopic structure, and will not be as effective if applied as a molecular dispersion. Release of a small topical dose of an anticholinergic drug may be more effective. Finally, providing antibiotic activity can be accomplished by moisture or pH-triggered release of a germicide which will dissolve in the sweat and kill the staph germs principally responsible for bodily odors.

The present invention is not intended to be limited by the specific implementations described above, nor by the specific examples used, but only by the claims appearing below.

We claim:

1. A process for release of guest molecules initially confined by physical entrapment in dendrimer host molecules, comprising fragmenting the host molecules by exposing them to electromagnetic radiation and producing a product comprising freed guest molecules and host molecule fragments.

2. The process of claim 1, wherein the electromagnetic radiation comprises photons having sufficient energy to trigger a bond-breaking reaction within the host molecules, leading to non-thermally fragmenting the host molecules.

3. The process of claim 1, further comprising a chemical reaction between the freed guest molecules and the host molecule fragments.

4. A dendrimer host molecule, comprising at least one chemical structure capable of confining a guest molecule by physical entrapment, which host molecule is convertible to molecular fragments by the action of electromagnetic radiation thereon, at least one of said at least one chemical structure being thereby rendered incapable of confining a guest molecule.

5. The host molecule of claim 4, further comprising at least one confined guest molecule.

6. The host molecule of claim 5, wherein some of the at least one confined guest molecule exhibit a desired active property.

7. The host molecule of claim 6, wherein the desired active property is pharmacological activity.

8. The host molecule of claim 7, wherein the desired active property is anticancer activity.

9. The host molecule of claim 7, wherein the desired active property is antibiotic activity.

10. The host molecule of claim 7, wherein the desired active property is antiviral activity.

11. The host molecule of claim 6, wherein the desired active property is herbicidal activity.

12. The host molecule of claim 6, wherein the desired active property is pesticidal activity.

* * * * *